United States Patent [19]

Cole

[11] Patent Number: 5,026,369

[45] Date of Patent: Jun. 25, 1991

[54] NON-INVASIVE METHOD OF REMOVING HAIR THROUGH ELECTROLYSIS

[76] Inventor: Hubert L. Cole, 160 S. May St., Southern Pines, N.C. 28387

[21] Appl. No.: 487,917

[22] Filed: Mar. 5, 1990

[51] Int. Cl.⁵ ............................................. A61B 17/38
[52] U.S. Cl. ......................................... 606/36; 606/43
[58] Field of Search .................................... 606/36, 43

[56] References Cited

U.S. PATENT DOCUMENTS

| | | | |
|---|---|---|---|
| 4,317,450 | 3/1982 | Chalmers et al. | 606/36 |
| 4,498,474 | 2/1985 | Chalmers et al. | 606/36 |

Primary Examiner—Lee S. Cohen
Attorney, Agent, or Firm—Rhodes, Coats & Bennett

[57] ABSTRACT

The present invention relates to a method for removing hair from a person through electrolysis. The method of the present invention is totally non-invasive in as much as the patient's skin is never penetrated by a needle or the like. After cleaning a particular hair to be removed, it is bathed in an electrode solution. Thereafter, a conductor is actually attached to the remote end of the treated hair. Then, current is directed along the treatment solution to the soft moist tissue surrounding the hair within the skin of the patient. Current is directed into the soft moist tissue and downwardly to the hair follicle. The current reaches the salt water content with the hair follicle and this results in the hair follicle undergoing a decomposition process. After a selected time period of decomposition, the hair can be removed from the patient.

10 Claims, 1 Drawing Sheet

NON-INVASIVE METHOD OF REMOVING HAIR THROUGH ELECTROLYSIS

FIELD OF THE INVENTION

The present invention relates to the field of removing hair through the process electrolysis.

BACKGROUND OF THE INVENTION

Hair removal through electrolysis has been performed for many years, and through this process women and others have been able to selectively remove hair from certain body areas. Essentially this hair removal process has been carried out by inserting a needle charged with a current into the hair follicle. This obviously can be a very painful process.

In the early stages of electrolysis there was much confusion and speculation as to why the process worked. Some investigators, for example, postulated that the hair follicle was "electrocuted". Later, it was determined that the process worked because of electrolytic action which gave rise to chemical decomposition in the hair follicle.

Now, the process of electrolysis as it relates to hair removal is very well understood. Within the hair follicle, there is found a solution of salt water and it is that solution of salt water that enables the electrolysis process to work. Essentially, by subjecting the salt water solution to an electrical current results in the salt, NaCl and the water, $H_2O$, breaking into their constituent chemical elements. This process is referred to as electrolysis and the subsequent rearrangement of the basic elements of salt and water is referred to as ionization. The new compound that is formed as a result of the ionization is sodium hydroxide, NaOH. The produced sodium hydroxide is highly caustic to the hair follicle and causes the same to die through a decomposition process. After the hair follicle has decomposed, the hair can be removed by a simple extraction process.

As pointed out above, hair removal through a conventional electrolysis process where the skin is actually penetrated with a current caring needle is very painful and slow. Therefore, there is a need for a less painful and more efficient process for removing unwanted hair.

SUMMARY AND OBJECTS OF THE PRESENT INVENTION

The present invention relates to an electrolysis process for removing hair that is non-invasive. The present process is non-invasive in as much as the process does not entail penetrating the patient's skin. Essentially, the present electrolysis process entails conducting an electric current via the electrode solution which coats the hair shaft so that the current is directed to the soft moist tissue surrounding the hair shaft about the surface of the skin from which the current is directed on down into the hair follicle itself. Upon reaching the hair follicle, the current gives rise to electrolysis, resulting in the production of sodium hydroxide. The production of sodium hydroxide results in the hair follicle going through a decomposition process. The general epithelium of the follicle is killed, rendering that follicle unable to ever produce another hair. After the current has been directed to the hair follicle, the hair is allowed to stand for a selected time period, after which the hair is extracted.

Thus, it is appreciated that in the present invention, the process of electrolysis is carried out by utilizing the electrode solution as a medium for conducting current to the hair follicle. As will be appreciated from reviewing the present disclosure, an electrode solution is applied to the hair prior to directing the current along the hair. This is important since the hair itself is not a good conductor of electricity.

It is therefore an object of the present invention to provide an efficient and painless electrolysis method for removing hair.

Another object of the present invention resides in the provision of an electrolysis process that is non-invasive in as much as the patient's skin is not actually penetrated by a needle.

A further object of the present invention resides in the provision of a method of electrolysis through which hair can be removed wherein the process actually utilizes an electrode solution which coats the hair as a medium for conducting electricity into the skin of the patient and to the hair follicle.

Another object of the present invention entails an efficient electrolysis method that entails applying an electrode solution to a selected hair to be removed and then coupling that hair directly to an electrical source and transmitting a current through the electrode solution which coats the hair, and into the skin where the current is directed to the hair follicle.

A further object of the present invention resides in the provision of an electrolysis process of the character referred to above that is easy to use, reliable, and safe.

Other objects and advantages of the present invention will become apparent and obvious from a study of the following description and the accompanying drawings which are merely illustrative of such invention.

DETAILED DESCRIPTION OF THE INVENTION

Figure 1:
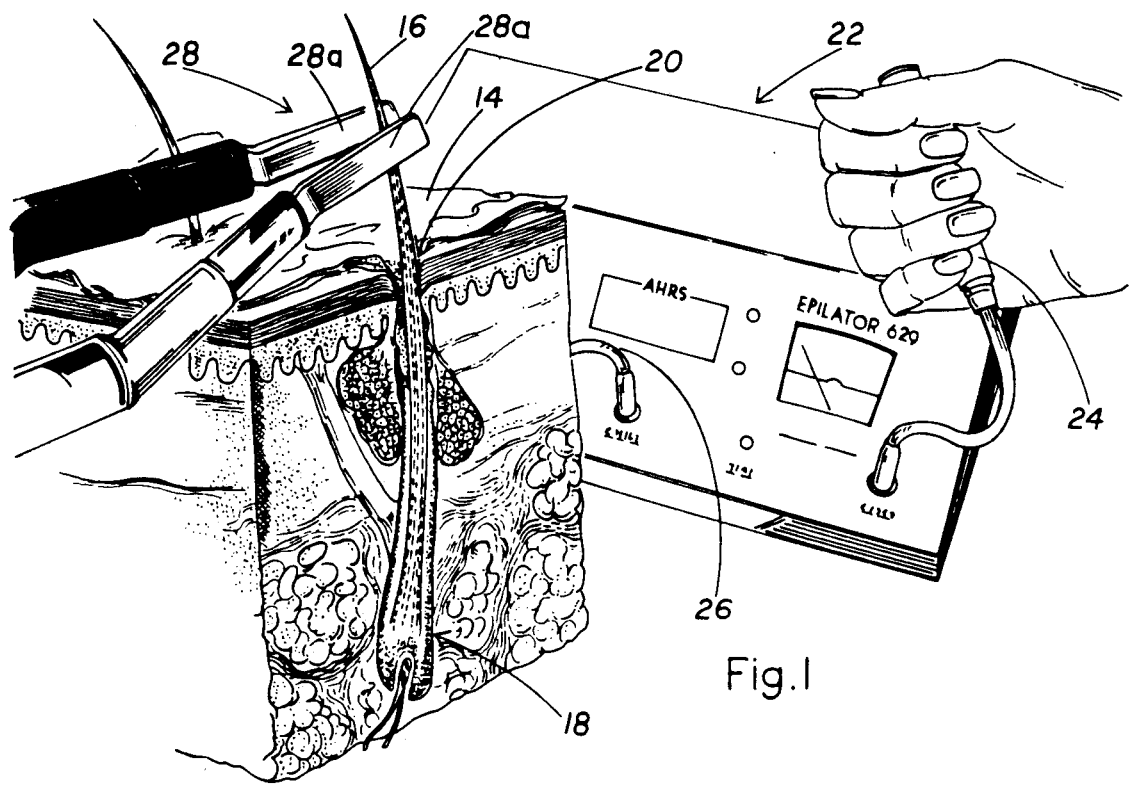
FIG. 1 is a schematic illustration showing the present electrolysis process and particularly showing that portion of the process where an electrical connector is connected directly to the hair to be removed.

With further reference to the drawings, the present electrolysis process is illustrated therein. Before proceeding with a discussion of the process itself, it will be beneficial to basically review the patient's body structure and the anatomy of the patient's hair. In this regard, the skin and hair structure of the patient is shown in a schematic or illustrative form. As shown in the drawings, the patient's skin surface is indicated by the numeral 14. Extending upwardly through the patient's skin surface 14 is any number of hairs or hair shafts 16. The basic hair shaft 16 extends downwardly through the skin of the patient and is anchored or set below the skin surface 14. The basic hair structure lying below the skin surface is referred to as the hair follicle and is indicated in the drawings generally by the numeral 18.

Surrounding hair shaft 16 about the surface of the skin 14 is what is referred to as soft moist tissue, and this is referred to by the numeral 20. As will be further understood from subsequent portions of this disclosure, the soft moist tissue 20 in the present process actually acts as a conductor of electrical current in the electrolysis process that forms a subject matter of the present invention.

To carry out the present process, it is required that there be a current source, and in the drawings this current source is indicated generally by the numeral 22. The device forming the current source 22 is a conventional current producing electrolysis device that has the capability of generating an electrical current having a relatively low current and high voltage (e.g. a current range of 0.10–1.00 ma and voltage of 350–400 volts). Details of the current source 22 are not dealt with here in detail because such is not per se material to the present invention, and because such devices have long been used and are commercially available today. For example, a typical current device of this type is manufactured by A. R. Hinkle of Sun Valley, Calif. and is referred to as model UC-2 Epilator.

Figure 2:
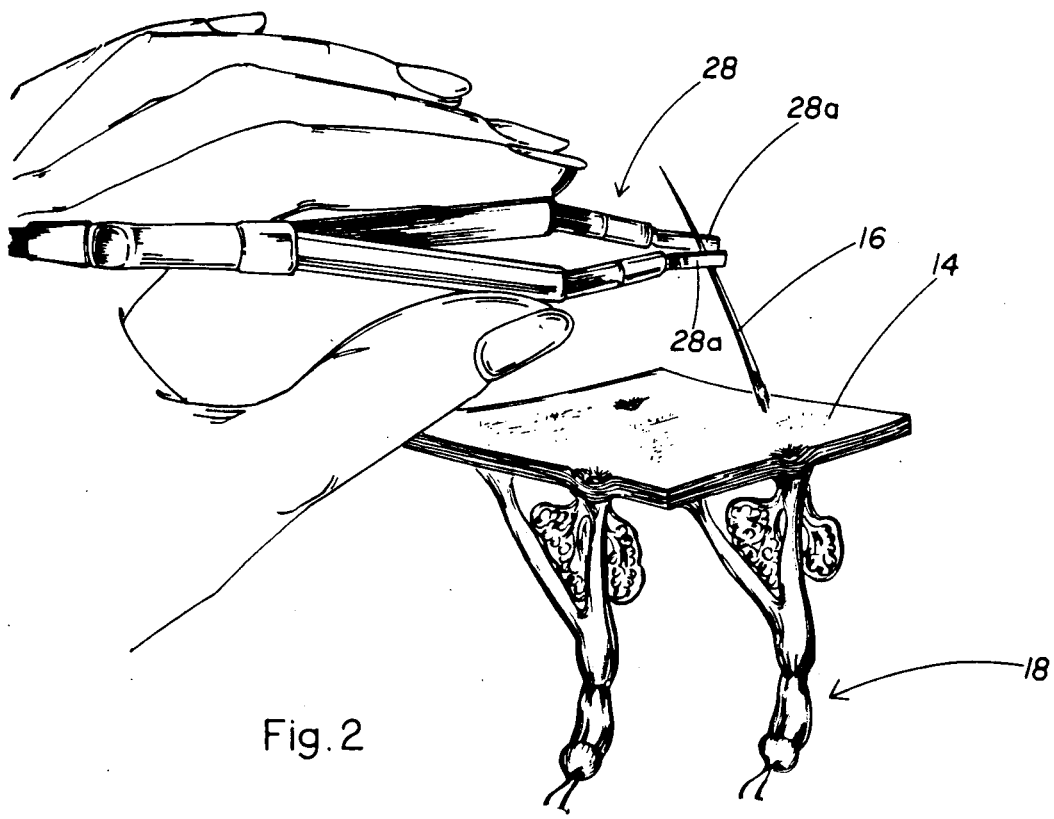
FIG. 2 is also an illustration showing the connection of an electrical conductor to a hair shaft to be removed.

In any event, the current source includes a ground device 24, that in the present case is simply a hand held conductor that is coupled to the current source 22. In addition, current source 22 includes a current line 26 that leads from the current source machine 22 and includes an electrical conductor 28 that is in the form of a hair connector. It is seen that hair connector 28 includes a tweezer end 28a that is operative to grasp a particular hair 16 to be removed. More particular, the hair connector 28 includes an insulated hand holding portion that is particularly illustrated in FIG. 2. Note that the insulated portion spaced from the tweezer 28 can be grasped between the thumb and forefinger. Because of the construction (e.g. spring steel) of the hair connector 28, the same is generally biased to assume an open non-connected position. By pressing the forefinger and thumb together, the hair connector 28 is closed resulting in the tweezer end 28 engaging and grasping the hair 16 to be removed.

Now turning to the particular process of the present invention, in the hair removal process, it is first important to clean the hair and skin area surrounding the hair. The importance of cleaning the skin and the hair to be removed can not be over stressed. A soap type cleaning solution is applied to the skin and the hair to be removed. The soap solution is rubbed onto the skin creating a lather and by applying slight pressure, the lather is rubbed onto the skin and the surrounding hair area. After thoroughly cleaning the skin and the hair to be removed, a damp towel is used to wipe off the cleaning solution.

Next, the individual hairs or the hair to be removed is treated with an electrode solution. The purpose of the electrode solution treatment process is to coat the hair or hairs to be removed with an electrode solution in order that electrical current can be transmitted along the electrode solution. This is important to the present process since the hair structure itself is not a good conductor of electricity.

In the present case, it is contemplated that the electrode solution would be a semigel, and in particular would be a saline type solution basically comprising glycerin. A typical electrode solution would comprise 85% by weight of glycerin, 14% by weight of water, 0.5% weight of salt, and 0.5% by weight of copper sulfate. As pointed out above, this solution would generally form a semi-gel type solution which can be applied to the hair or hairs to be removed.

After the particular hair to be removed has been thoroughly treated with the electrode saline solution, it is now appropriate to utilize the electrolysis process itself. Instead of actually penetrating the patient's skin with a charged or current caring needle, the present electrolysis process is totally non-invasive. The patient is asked to grasp the grounding device 24 with one hand. The hair connector 28 is connected to the outer remote end portion of a particular hair to be removed. Next, the current source 22 is actuated so as to direct an electrical current down the treated hair or hair shaft 16. In the present electrolysis process, the activating current is a DC current. The electrolysis process contemplates directing a 0.47 ma current through the patient at a voltage of approximately 380 volts. This small current is allowed to remain active for approximately twenty-four seconds at which time the current source is turned off and the patient effectively is disconnected from the current source. Thereafter, that particular hair is allowed to stand for approximately thirty minutes after which time that hair is extracted from the patient.

Referring back to the electrolysis process, in directing current to the patient, it should be pointed out that the electrode solution coating the hair shaft 16 acts as a conductor. The produced electrical current is transferred to the soft moist tissue 20 surrounding the hair 16 within the skin and body of the patient. From the moist tissue surrounding the hair, the current is directed downwardly to the base or anchor portion of the hair structure that is referred to as the hair follicle. It is this area of the hair structure that contains the salt water content. Once the electrical current reaches the salt water content found in the hair follicle, the electrolysis process begins. Essentially, the electrical current causes the salt (NaCl) and the water ($H_2O$) to break up into their constituent chemical elements. This produces sodium hydroxide (NaOH) which is highly caustic and which results in a decomposition process within the hair follicle. This resulting decomposition process causes the hair to die, and kills the germinal epithelium of the hair follicle and enables the same to be extracted.

The present electrolysis process is advantageous for the reasons set forth and is particularly advantageous in as much as it is totally non-invasive.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A non-invasive method of removing hair having a remote end from a patient by electrolysis, comprising the steps thereof:
    (a) cleaning an area of the patients skin having one or more hairs extending therefrom;
    (b) treating respective hairs to be removed by bathing them in an electrode solution;
    (c) electrically connecting a respective treated hair to an electrical source and directing an electrical current down the electrode solution coating the hair to the soft moist tissue surrounding hair within the skin;
    (d) producing sodium hydroxide (NaOH) at the hair follicle site by chemically reacting water and sodium chloride (NaCl) in the presence of the electrical current causing the germ cells forming a part of the hair follicle to die, resulting in the hair follicle decomposing and permitting the hair stemming from the hair follicle to be easily extracted; and (e) allowing the treated hair to remain in the hair follicle for at least approximately 30 minutes prior to pulling the treated hair from the hair follicle.

2. The method of claim 1 wherein in the step of electrically connecting the hair to the electrical source includes connecting a conductor directly to the remote end of the treated hair while appropriately grounding the patient.

3. The method of claim 2 wherein the electrical current directed along the electrode solution coating the hair to the soft tissue surrounding the hair within the skin area is a current of approximately 0.47ma having a voltage potential of approximately 380 volts.

4. The method of claim 3 wherein the current is directed along the electrode solution coating the hair and into the soft tissue surrounding the hair within the skin area for a time period of approximately twenty-four seconds.

5. The method of claim 4 wherein the step of treating the hair includes bathing the hair in an electrode solution including glycerin, water, salt, and copper sulfate.

6. The method of claim 5 wherein the electrode solution comprises a composition of glycerin, water, salt and copper sulfate wherein by weight the glycerin makes up approximately 85 percent of the composition while the water makes up approximately 14 percent of the composition, and wherein the salt and copper sulfate each make up approximately 0.5 percent of the composition.

7. A non-invasive method of removing hair through electrolysis from a patient comprising:

(a) treating a hair having a remote end extending from the patient by bathing the same in an electrode solution;

(b) connecting a conductor to the remote end portion of the hair to be removed;

(c) grounding the patient;

(d) directing electrical current along the electrode solution coating the hair into the soft moist tissue surrounding the hair such that the current ultimately reaches the salt water content of the associated hair follicle;

(e) producing sodium hydroxide (NaOH) at the hair follicle site by chemically reacting water and sodium chloride (NaCl) in the presence of the electrical current causing the germ cells forming a part of the hair follicle to die, resulting in the hair follicle decomposing and permitting the hair stemming from the hair follicle to be easily extracted; and (f) allowing the treated hair to remain in the hair follicle for at least approximately 30 minutes prior to pulling the hair from the decomposed hair follicle.

8. The method of claim 7 wherein the step of bathing the hair to be extracted with an electrode solution includes bathing that hair with a glycerin-water solution.

9. The method of claim 8 wherein the step of directing the current along the electrode solution coating the hair to be removed includes directing a relatively high voltage but small current along the hair for a selective time period.

10. The method of claim 9 wherein the electrode solution includes a composition comprising approximately 85% by weight glycerin, approximately 14% of weight of water, approximately 0.5% of salt, and approximately 0.5% by weight of copper sulfate.

* * * * *